United States Patent [19]

Tomita et al.

[11] Patent Number: 5,493,033
[45] Date of Patent: Feb. 20, 1996

[54] PROCESS FOR PURIFYING TETRACHLOROPHTHALIC ANHYDRIDE

[75] Inventors: Kyoichi Tomita; Zentaro Ueda, both of Shizuoka; Seiji Maekawa, Matsudo, all of Japan

[73] Assignee: Nippon Light Metal Company, Ltd., Tokyo, Japan

[21] Appl. No.: 252,459

[22] Filed: Jun. 1, 1994

[30] Foreign Application Priority Data

Jun. 2, 1993 [JP] Japan .................. 5-132186

[51] Int. Cl.$^6$ ................................ C07D 307/89
[52] U.S. Cl. ................................ 549/246
[58] Field of Search ........................ 549/246

[56] References Cited

U.S. PATENT DOCUMENTS

| | | | |
|---|---|---|---|
| 2,429,985 | 11/1947 | Blume et al. | 549/246 |
| 2,460,564 | 2/1949 | Amacker | 549/246 |
| 2,460,565 | 2/1949 | Amacker | 549/246 |
| 2,547,504 | 4/1951 | Steahly | 549/246 |
| 2,547,505 | 4/1951 | Steahly | 549/246 |
| 3,007,943 | 11/1961 | Hoffmann | 549/246 |

FOREIGN PATENT DOCUMENTS

| | | | |
|---|---|---|---|
| 1934174 | 1/1971 | Germany . | |
| 38-25365 | 11/1963 | Japan . | |
| 60-161974 | 8/1985 | Japan . | |
| 61-118378 | 6/1986 | Japan . | |
| 61-118378 | 6/1986 | Japan . | |
| 62-185082 | 8/1987 | Japan . | |
| 62-185082 | 8/1987 | Japan | 549/246 |
| 1719401 | 3/1992 | Russian Federation | 549/246 |
| 825497 | 4/1981 | U.S.S.R. | 549/246 |
| 823507 | 11/1959 | United Kingdom . | |
| 958294 | 5/1964 | United Kingdom | 549/246 |

OTHER PUBLICATIONS

"Monthly Journal of Chemistry and Related Areas of Other Sciences", vol. 64, Aug. 1934.
"Studies of Chlorination, Principally to Obtain Tetrachlorophthalic Anhydride, Pentachlorobenzoic Acid and a New (Tetrachlorophenyl)Trichloromethane", Chemical Abstracts, vol. 45, No. 2, 1951.
"The Synthesis of Tetrachlorophthalic Anhydride" Chemical Abstracts, vol. 55, No. 2, 1961.

*Primary Examiner*—Cecilia Tsang
*Attorney, Agent, or Firm*—Birch, Stewart, Kolasch & Birch

[57] ABSTRACT

In the purification of crude tetrachlorophthalic anhydride containing hexachlorobenzene as impurities, this invention relates to purification by decomposition in which crude tetrachlorophthalic anhydride is contacted with chlorine gas in fuming sulfuric acid or sulfuric anhydride in the presence of iodine or iodine trichloride to decompose the impurities and remove them or purification by washing in which hexachlorobenzene is separated by washing with a chlorinated solvent. This invention also relates to a process for purifying crude tetrachlorophthalic anhydride containing iodotrichlorophthalic anhydrides as impurities by applying a radical reaction treatment in a chlorinated solvent to convert iodotrichlorophthalic anhydrides to tetrachlorophthalic anhydride. Moreover, it relates to high-purity tetrachlorophthalic anhydride containing 10 ppm or less of hexachlorobenzene. With the process of this invention, it is possible to recover high-purity tetrachlorophthalic anhydride with extremely low contents of impurities readily in high yield.

8 Claims, No Drawings

PROCESS FOR PURIFYING TETRACHLOROPHTHALIC ANHYDRIDE

FIELD OF THE INVENTION AND RELATED ART STATEMENT

This invention relates to a purifying process for obtaining high-purity tetrachlorophthalic anhydride, and, particularly, to a process for purifying crude tetrachlorophthalic anhydride which contains harmful hexachlorobenzene and/or unwanted iodotrichlorophthalic anhydrides as impurities and yielding high-purity tetrachlorophthalic anhydride with the contents of these impurities reduced as much as possible. In particular, this invention relates to high-purity tetrachlorophthalic anhydride with an extremely low content of hexachlorobenzene.

Tetrachlorophthalic anhydride finds a wide variety of uses such as raw materials for perione dyes and quinophthalone dyes which are useful for coloring resins, raw materials for isoindolinone pigments and phthalocyanine pigments which are useful for coatings and printing inks and flame retardants for multipurpose synthetic resins such as polyesters, polyurethanes and polyols.

The following processes are known mainly for the manufacture of tetrachlorophthalic anhydride: a vapor-phase chlorination process in which phthalic anhydride is contacted with chlorine gas in the vapor phase [Japan Tokkyo Koho No. Sho 38-25,365 (1963), Japan Kokai Tokkyo Koho No. Sho 60-161,974 (1985) and Japan Kokai Tokkyo Koho No. Sho 62- 185,082 (1987)]; a liquid-phase chlorination process in which phthalic anhydride is contacted with chlorine gas in a solvent [Japan Kokai Tokkyo Koho No. 61-118,378 (1986) and West German Patent No. 1,934,174]; and a chlorination process in which naphthalene is contacted with chlorine gas in a solvent [Walter, Monatsh. Chem. Vol. 64, p 287 (1934), West Germany].

Of the processes cited above, a manufacturing process based on the vapor-phase process inevitably produces a variety of chlorinated byproducts in the course of reaction and, as described in the cited literature, some of such byproducts mainly consist of polychlorobenzenes which are regarded harmful to the human body as exemplified by hexachlorobenzene (HCB).

In consequence, whenever tetrachlorophthalic anhydride containing the aforesaid byproducts as impurities is used directly as additives to synthetic resins, for example, as flame retardants or as intermediates for the manufacture of dyes and pigments, the final commercial products such as resins, dyes and pigments become contaminated with these byproducts. The contaminated products are restricted in usage under a variety of official regulations and, particularly in the fields related to food packaging, it has been necessary either to abondon their use or to purify them by a special process before putting them to practical use.

In a manufacturing process based on the liquid-phase process, the reaction is carried out in a chlorosulfonic acid as solvent in the presence of iodine or an iodine chloride as catalyst. This process produces less byproducts such as HCB than the above-mentioned vapor-phase process and the product tetrachlorophthalic anhydride becomes contaminated less with the byproducts. However, the contamination by HCB here may be on the order of 100 to 1,000 ppm, occasionally 500 to 2,000 ppm.

According to a knowledge acquired by the present inventors, the manufacture of tetrachlorophthalic anhydride by the above-mentioned liquid-phase process produces iodochlorophthalic anhydrides as byproducts, which result from partial substitution of the chlorine atoms in tetrachlorophthalic anhydride with iodine atoms probably because of the use of iodine or an iodine chloride as catalyst and which have not received attention as impurities. It has been proved, in particular, that iodotrichlorophthalic anhydrides of the following formula form as a result of the substitution of 1- or 2-chlorine atom with an iodine atom and these impurities contaminate tetrachlorophthalic anhydride to an extent of 0.1 to 3% by weight.

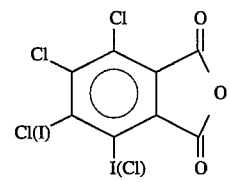

The formation of iodotrichlorophthalic anhydrides increases markedly when the reaction temperature is 100° C. or less and the use of tetrachlorophthalic anhydride containing these impurities as reaction feed contributes to an increased output of byproducts derived from the impurities.

In addition, it has been extremely difficult to suppress the formation of these byproducts in the course of the reaction by control of the reaction conditions or to prevent the byproducts from contaminating the product tetrachlorophthalic anhydride in either of the above-mentioned vapor-phase and liquid-phase processes. Although it is possible to reduce the amount of the byproducts by conventional means for purification such as recrystallization, this approach has a limit and encounters the problem of markedly reduced yields of tetrachlorophthalic anhydride with an attendant increase in production cost.

OBJECT AND SUMMARY OF THE INVENTION

The present inventors have conducted extensive studies on a purifying process which yields high-purity tetrachlorophthalic anhydride with extremely low contents of harmful HCB and/or unwanted iodotrichlorophthalic anhydrides and completed this invention.

It is therefore an object of this invention to provide a process for purifying tetrachlorophthalic anhydride which is capable of purifying crude tetrachlorophthalic anhydride containing harmful or unwanted substances such as HCB and/or iodotrichlorophthalic anhydrides as impurities and recovering high-purity tetrachlorophthalic anhydride with extremely low contents of these impurities readily in high yield.

Another object of this invention is to provide a process for purifying tetrachlorophthalic anhydride which purifies the reaction products formed in the chlorination of phthalic acid, phthalic anhydride or naphthalene and recovers high-purity tetrachlorophthalic anhydride with extremely low contents of harmful or unwanted substances such as HCB and/or iodotrichlorophthalic anhydrides.

A further object of this invention is to provide high-purity tetrachlorophthalic anhydride with a hexachlorobenzene content of 10 ppm or less.

This invention thus relates to a process for purifying crude tetrachlorophthalic anhydride containing hexachlorobenzene as impurities which comprises either purification by decomposition in which crude tetrachlorophthalic anhydride is brought into contact with chlorine gas in fuming sulfuric acid or sulfuric anhydride as solvent in the presence of iodine or iodine trichloride to decompose said impurities and remove them or purification by washing in which crude tetrachlorophthalic anhydride is washed with a chlorinated solvent to separate and remove hexachlorobenzene.

This invention also related to a process for purifying crude tetrachlorophthalic anhydride containing iodotrichlorophthalic anhydrides as impurites which comprises subjecting crude tetrachlorophthalic anhydride to a radical reaction treatment in a chlorinated solvent thereby converting the iodotrichlorophthalic anhydrides to tetrachlorophthalic anhydride.

This invention further relates to a process for purifying tetrachlorophthalic anhydride which comprises purifying the reaction products obtained in the chlorination of phthalic acid, phthalic anhydride or naphthalene and recovering high-purity tetrachlorophthalic anhydride with extremely low contents of harmful or unwanted substances such as HCB and iodotrichlorophthalic anhydrides.

Still further, this invention relates to high-purity tetrachlorophthalic anhydride with a hexachlorobenzene content of 10 ppm or less.

The process for purifying tetrachlorophthalic anhydride of this invention purifies crude tetrachlorophthalic anhydride which results from the chlorination of phthalic acid, phthalic anhydride or naphthalene and contains harmful or unwanted substances such as HCB and iodotrichlorophthalic anhydrides as impurities, removes these impurities as much as possible and recovers high-purity tetrachlorophthalic anhydride. The crude tetrachlorophthalic anhydride here may be the one obtained by the vapor-phase or liquid-phase process or the one purified thereafter to some extent or it may be the unpurified reaction products obtained by a posttreatment of the reaction mixture from the chlorination of phthalic acid, phthalic anhydride or naphthalene.

In the process of this invention for purification by decomposition which decomposes and removes hexachlorobenzene in crude tetrachlorophthalic anhydride, fuming sulfuric acid or sulfuric anhydride to be used therein contains free sulfur trioxide in the range from 10 to 80% by weight or is sulfur trioxide itself. When crude tetrachlorophthalic anhydride is brought into contact with chlorine gas in such fuming sulfuric acid or sulfuric anhydride as solvent in the presence of iodine or iodine trichloride which acts as catalyst, the impurities in crude tetrachlorophthalic anhydride, particularly HCB, undergo selective decomposition and become soluble in the solvent for easy removal.

The quantity of fuming sulfuric acid or sulfuric anhydride as solvent is normally 1 to 20 liters, preferably 5 to 15 liters, per 1 kg of crude tetrachlorophthalic anhydride. A quantity of less than 1 liter of the solvent per 1 kg of crude tetrachlorophthalic anhydride causes difficulties in agitation and slows down the reaction while a quantity of more than 20 liters requires a larger reaction volume and is not practical.

The quantity of iodine or iodine trichloride which is used with the aforesaid solvent, fuming sulfuric acid or sulfuric anhydride, and acts as catalyst is in the range from 0.1 to 10% by weight as iodine, preferably from 0.5 to 5% by weight, in the purification system. If the catalyst becomes less than 0.1% in quantity in the purification system, some of the catalyst leaves the reaction solvent by sublimation and slows down the reaction. On the other hand, more iodotrichlorophthalic anhydrides form if more than 10% of the catalyst is present. There is no restriction to the way the catalyst is added to the purification system and the catalyst may be added in whole at the start of the treatment or in several portions at the start, halfway and later in the course of the reaction.

The temperature in the above-mentioned purification by decomposition is normally set in the range from room temperature to 150° C., preferably from 50° to 100° C., in order to decompose HCB present in crude tetrachlorophthalic anhydride. Heating above 150° C. is undesirable as it induces the decomposition of tetrachlorophthalic anhydride and reduces the recovery of this compound. A treatment performed at a temperature in the range from 50° to 100° C. can selectively decompose HCB at high efficiency while suppressing the decomposition of tetrachlorophthalic anhydride.

Thus, a sequence of contacting crude tetrachlorophthalic anhydride with chlorine gas in fuming sulfuric acid or sulfuric anhydride in the presence of iodine or iodine trichloride, separating crystals by cooling and recovering the crystals by filtration, washing with water and drying yields high-purity tetrachlorophthalic anhydride with the content of HCB reduced as much as possible.

In the preparation of tetrachlorophthalic anhydride with application of the purification by decomposition of this invention, it is preferable to carry out the chlorination of phthalic acid, phthalic anhydride or naphthalene in fuming sulfuric acid or sulfuric anhydride as solvent, use the reaction mixture without isolation of the reaction products therefrom as crude tetrachlorophthalic anhydride in the above-mentioned purification by decomposition, add iodine or iodine trichloride as catalyst to the reaction mixture and continue the treatment. In this manner, it becomes unnecessary to carry out an after treatment of the reaction mixture to take out the reaction product tetrachlorophthalic anhydride and this simplifies the procedure and increases the yield.

In the purification by washing of this invention to separate HCB from crude tetrachlorophthalic anhydride, the chlorinated solvents therefor have one or more chlorine atoms, preferably two or more, more preferably three or more, and they include one compound or a mixture of two or more compounds selected from carbon tetrachloride, ethylene tetrachloride, butadiene hexachloride and benzotrichloride.

The chlorinated solvent is normally used 1 to 100 times by weight, preferably 10 to 50 times by weight, of crude tetrachlorophthalic anhydride. Less than 1 times by weight cannot perform stable removal of the impurities while more than 100 times by weight reduces recovery as more products dissolve in the solvent.

The purification by washing is carried out, for example, by adding crude tetrachlorophthalic anhydride to a chlorinated solvent, heating with stirring to the specified temperature to accelerate the dissolution of HCB in the solvent, cooling the solution, filtering the separated crystals, washing the crystals further with a chlorinated solvent, preferably the same solvent as used initially, and drying the crystals. The temperature for the purification by washing is normally in the range from 50° to 150° C., preferably from 80° to 120° C. The removal of HCB becomes insufficient at a temperature lower than 50° C. while purified tetrachlorophthalic anhydride undergoes discoloration at a temperature in excess of 150° C.

It is conceivable that tetrachlorophthalic anhydride partly dissolves in the chlorinated solvent when heated with stirring to the specified temperature and recrystallizes when cooled and HCB with a higher solubility remains dissolved in the solvent and removed. Therefore, in the cases where the purification by washing follows the radical reaction treatment in a chlorinated solvent, heating applied only in the radical reaction treatment would produce the same effect as if heating were also applied in the purification by washing.

In the radical reaction treatment of crude tetrachlorophthalic anhydride containing iodotrichlorophthalic anhydrides as impurities according to the purifying process of this invention, the chlorinated solvents therefor may be identical with those in the above-mentioned purification by washing and they are used normally 1 to 100 times by weight, preferably 10 to 50 times by weight, of crude tetrachlorophthalic anhydride. Less than 1 times by weight retards the reaction and also causes difficulties in agitation while more than 100 times by weight becomes not practical as it requires a larger reaction volume.

In the radical reaction treament to be carried out in a chlorinated solvent, a means such as photoirradiation and addition of radical reaction initiators is adopted in order to generate radicals. Photoirradiation is preferable as radical reaction initiators themselves may be a new source of impurities. High-pressure mercury-vapor lamps are normally used in photoirradiation.

The reaction system in the radical reaction treatment by photoirradiation is a dispersion of crude tetrachlorophthalic anhydride in a chlorinated solvent and it is desirable to stir, preferably also to heat, the dispersion in order to obtain improved participation of the light in the reaction. The photoirradiation here is effected at a wavelength of 3,000 Å or more for a period of 5 to 20 hours and the reaction temperature is in the range from room temperature to 150° C., preferably from 50° to 120° C. Under the photoirradiation conditions deviating from those specified above, problems such as discoloration and decomposition arise. On the other hand, heating at a temperature in excess of 150° C. is undesirable as it induces the decomposition of tetrachlorophthalic anhydride and reduces the product recovery. As long as the reaction temperature is held in the range from 50° to 100° C., iodotrichlorophthalic anhydrides are converted to tetrachlorophthalic anhydride at high efficiency while the decomposition of tetrachlorophthalic anhydride is suppressed.

Where this invention deals with crude tetrachlorophthalic anhydride containing HCB and iodotrichlorophthalic anhydrides as impurities, the purification by decomposition is applied by contacting crude tetrachlorophthalic anhydride with chlorine gas in fuming sulfuric acid or sulfuric anhydride in the presence of iodine or iodine trichloride to decompose and remove the HCB or the purification by washing is applied to separate the HCB by washing with a chlorinated solvent and, as needed, the solvent is changed from fuming sulfuric acid or sulfuric anhydride to a chlorinated solvent and the radical reaction treatment is applied in the chlorinated solvent to convert the iodotrichlorophthalic anhydrides to tetrachlorophthalic anhydride.

The procedures described above may be applied here to the purification by decomposition and the purification by washing of HCB or the radical reaction treatment for the conversion of iodotrichlorophthalic anhydrides to tetrachlorophthalic anhydride.

Simultaneous use of the purification by decomposition and the purification by washing of HCB or the radical reaction treatment of iodotrichlorophthalic anhydrides can remove as much as possible of both HCB and iodotrichlorophthalic anhydrides which are byproducts in the production of iodotrichlorophthalic anhydride by the chlorination of phthalic acid, phthalic anhydride or naphthalene and yield high-purity tetrachlorophthalic anhydride with extremely low contents of these harmful or unwanted substances.

Tetrachlorophthalic anhydride obtained by the applicaton of the purifying process of this invention contains normally 10 ppm or less, preferably 5 ppm or less, of HCB and 500 ppm or less, preferably 100 ppm or less, of iodotrichlorophthalic anhydrides and is extremely pure in respect to these harmful and unwanted substances.

In the purification by decomposition of this invention where crude tetrachlorophthalic anhydride is contacted with chlorine gas in fuming sulfuric acid or sulfuric anhydride in the presence of iodine or iodine trichloride, it is likely that HCB present in crude tetrachlorophthalic anhydride is decomposed into chloranil (tetrachloro-p-benzoquinone) which is soluble in the solvent (fuming sulfuric acid or sulfuric anhydride) and easy to remove and this makes it possible to remove the impurities at high efficiency.

On the other hand, in the purification by washing where crude tetrachlorophthalic anhydride is washed with a chlorinated solvent to remove HCB, the impurities are considered to have high solubility in chlorinated solvents.

In the radical reaction treatment where crude tetrachlorophthalic anhydride is radically treated in a chlorinated solvent for the conversion of iodotrichlorophthalic anhydrides to tetrachlorophthalic anhydride, the iodine atoms in iodotrichlorophthalic anhydrides are extracted to generate trichlorophthalic anhydride radicals and the radicals react with the chlorine atoms in a chlorinated solvent. The net result is the replacement of the iodine atoms in iodotrichlorophthalic anhydrides with the chlorine atoms in a chlorinated solvent.

This invention thus makes it possible to purify crude tetrachlorophthalic anhydride containing harmful or unwanted substances such as HCB and iodotrichlorophthalic anhydrides and yield high-purity tetrachlorophthalic anhydride with extremely low contents of these harmful substances.

Moreover, tetrachlorophthalic anhydride obtained by the process of this invention contains 10 ppm or less of HCB. With this much low content of the harmful substances, tetrachlorophthalic anhydride contributes to improve the product safety when used as raw materials in the production of synthetic resins, dyes and pigments and also improve the safety when these products are applied to packagings and printings, particularly to areas related to food packaging.

Iodotrichlorophthalic anhydrides occurring as impurities have not been confirmed yet as to their harmfulness, but they are unwanted substances in any case. Tetrachlorophthalic anhydride containing 500 ppm or less of these impurities is available, and the use of this product as raw material contributes to reduce the quantity of byproduct impurities as much as possible.

DETAILED DESCRIPTION OF THE PREFERRED EMBODIMENTS

This invention will be described in detail below with reference to the accompanying examples.

The purity of tetrachlorophthalic anhydride and the contents of HCB and iodotrichlorophthalic anhydrides in tetrachlorophthalic anhydride were determined as follows.

[Determination of the purity of tetrachlorophthalic anhydride]

A sample weighing 0.2 g was dissolved in 10 ml of toluene, 1 μl of the solution was analyzed by GC (gas chromatography) with the aid of a gas chromatograph, Model GC-14A, manufactured by Shimadzu Corporation and the purity was calculated from the area under the signal peak on the chromatogram.

[Determination of the content of HCB]

A sample weighing 40 mg was added to 5 ml of toluene, the mixture was shaken vigorously and left standing and 1 μl of the supernatant liquid was analyzed quantitatively by GC-MS (gas chromatography-mass spectrometry) with the aid of a GC-MS analyzer, Model GC-MS3970A, manufactured by HP with reference to a standard calibration curve prepared in the same manner.

[Determination of the content of iodotrichlorophthalic anhydrides]

The determination was made in the same manner as for the purity of tetrachlorophthalic anhydride.

EXAMPLE 1

Into a glass reactor fitted with a reflux condenser, a thermometer, an inlet tube for chlorine gas and a stirrer were introduced 200 g of fuming sulfuric acid (concentration of free $SO_3$, 25%) as solvent and 2.01 g of crude tetrachlorophthalic anhydride containing HCB (100 ppm) and iodotrichlorophthalic anhydrides (0.9%), the mixture was heated with stirring up to 70° C., 0.10 g of iodine was added and the mixture was stirred for 5 hours with introduction of chlorine gas at a rate of 0.8 g/min to effect the purification by decomposition of HCB. The quantity of chlorine introduced into the treating system during this time was 120 g in total.

Upon completion of the purification by decomposition of HCB, the treated product was filtered by suction, washed with a small amount (5 ml) of water and dried to yield 1.62 g of tetrachlorophthalic anhydride.

The tetrachlorophthalic anhydride thus obtained contained 12.5 ppm of HCB and 0.8% by weight of iodotrichlorophthalic anhydrides as residual impurities.

Into a glass reactor were introduced 1.62 g of the tetrachlorophthalic anhydride obtained above and 20 ml of ethylene tetrachloride and the mixture was subjected to the radical reaction treatment by heating it at 100° C. with stirring and irradiating it with a high-pressure mercury-arc lamp (wavelength: 3,000 Å or more) for 10 hours.

Upon completion of the radical reaction treatment, the reaction mixture was cooled to 20° C., filtered, washed with 5 ml of ethylene tetrachloride and dried to yield 1.43 g (recovery 70.1%) of purified tetrachlorophthalic anhydride in powder.

The purified tetrachlorophthalic anhydride thus obtained was examined for the contents of HCB and iodotrichlorophthalic anhydrides, which were 1.9 ppm and 0.05% respectively.

EXAMPLE 2

Into a 50-ml round-bottomed flask fitted with a reflux condenser and a thermometer were introduced 0.4607 g (1.611 mmol) of crude tetrachlorophthalic anhydride containing 14 ppm of HCB and 10 ml of carbon tetrachloride as solvent and the mixture was subjected to the purification by washing of HCB by heating it at 80° C. with stirring for 8.0 hours.

Upon completion of the purification by washing, the treated liquor was cooled to 20° C., filtered by suction, washed with a small amount of carbon tetrachloride and dried to yield 0.4077 g (1.426 mmol, recovery 88.5%) of purified tetrachlorophthalic anhydride in white powder.

The purified tetrachlorophthalic anhydride contained 1.9 ppm of HCB.

EXAMPLE 3

The purification by washing of HCB was carried out as in Example 2 described above except introducing 0.5518 g (1.930 mmol) of crude tetrachlorophthalic anhydride containing 14 ppm of HCB and 10 ml of tetrachloroethylene as solvent and heating the mixture at 100° C.

The treated liquor was filtered by suction and the solid was washed with a small amount of tetrachloroethylene and dried to yield 0.4827 g (1.688 mmol, recovery 87.5%) of purified tetrachlorophthalic anhydride in white powder. The purified tetrachlorophthalic anhydride contained 1.3 ppm of HCB.

EXAMPLE 4

The purification by washing of HCB was carried out as in Example 2 described above except introducing 0.4876 g (1.705 mmol) of crude tetrachlorophthalic anhydride containing 14 ppm of HCB and 10 ml of hexachloro-1,3-butadiene as solvent and heating the mixture at 100° C.

The treated liquor was filtered by suction and the solid was washed with a small amount of hexachloro-1,3-butadiene and dried to yield 0.4667 g (1.632 mmol, recovery 95.7%) of purified tetrachlorophthalic anhydride in white powder. The purified tetrachlorophthalic anhydride contained 2.2 ppm of HCB.

EXAMPLE 5

Into a 50-ml round-bottomed flask fitted with a reflux condenser and a thermometer were introduced 0.5288 g (1.850 mmol) of crude tetrachlorophthalic anhydride containing 14 ppm of HCB and 0.9% of iodotrichlorophthalic anhydrides and 10 ml of carbon tetrachloride as solvent and the mixture was subjected to the radical reaction treatment by heating it with stirring at 76° C. and irradiating it with a high-pressure mercury-arc lamp (wavelength: 3,000 Å or more) for 8 hours. The reaction liquor was turned reddish violet by liberated iodine.

Upon completion of the radical reaction treatment, the reaction mixture was cooled to 20° C., filtered, washed with 10 ml of carbon tetrachloride and dried to yield 0.4698 g (1.644 mmol, recovery 88.8%) of purified tetrachlorophthalic anhydride in powder.

The purified tetrachlorophthalic anhydride thus obtained was examined for the contents of HCB and iodotrichlorophthalic anhydrides, which were 3.6 ppm and 0.22% respectively.

EXAMPLE 6

The purification by washing and the radical reaction treatment were carried out as in Example 5 except introducing 0.4802 g (1.680 mmol) of the same crude tetrachlorophthalic anhydride as used in Example 5 and 10 ml of ethylene tetrachloride as solvent and heating at 100° C. The reaction liquor was turned reddish violet by liberated iodine as in Example 5.

The purified tetrachlorophthalic anhydride thus obtained weighed 0.4170 g (1.459 mmol, recovery 86.8%) and contained 2.4 ppm of HCB and 0.10% of iodotrichlorophthalic anhydrides.

EXAMPLE 7

The purification by washing and the radical reaction treatment were carried out as in Example 5 except introducing 0.5015 g (1.754 mmol) of the same crude tetrachlorophthalic anhydride as used in Example 5 and 10 ml of hexachlorobutadiene as solvent and heating at 100° C. The reaction liquor was turned reddish violet by liberated iodine as in Example 5.

The purified tetrachlorophthalic anhydride thus obtained weighed 0.4533 g (1.585 mmol, recovery 90.4%) and contained 3.9 ppm of HCB and 0.04% of iodotrichlorophthalic anhydrides.

What is claimed is:

1. A process for purifying crude tetrachlorophthalic anhydride containing hexachlorobenzene impurities, comprising contacting said crude tetrachlorophthalic anhydride with chlorine gas in fuming sulfuric acid or sulfuric anhydride as solvent in the presence of iodine or iodine trichloride, at a temperature ranging from room temperature to 150° C., wherein the quantity of fuming sulfuric acid or sulfuric anhydride is 1 to 20 liters per 1 kg of crude tetrachlorophthalic anhydride and the quantity of iodine or iodine trichloride is 0.1 to 10% by weight as iodine based on the total weight of the reactants, and decomposing and removing said impurities.

2. A process for purifying crude tetrachlorophthalic anhydride containing hexachlorobenzene impurities, comprising washing said crude tetrachlorophthalic anhydride with a chlorinated solvent that is one or a mixture of two or more compounds selected from the group consisting of carbon tetrachloride, ethylene tetrachloride, hexachlorobutadiene and benzotrichloride, in an amount ranging from 1 to 100 times by weight of crude tetrachlorophthalic anhydride, at a temperature ranging from 50° to 150° C., and separating and removing said impurities.

3. A process for purifying crude tetrachlorophthalic anhydride containing iodotrichlorophthalic anhydride impurities, comprising subjecting said crude tetrachlorophthalic anhydride to a radical reaction treatment in a chlorinated solvent that is one or a mixture of two or more compounds selected from the group consisting of carbon tetrachloride, ethylene tetrachloride, hexachlorobutadiene and benzotrichloride, in an amount ranging from 1 to 100 times by weight of crude tetrachlorophthalic anhydride, at a temperature ranging from room temperature to 150° C., to convert said iodotrichlorophthalic anhydride impurities to tetrachlorophthalic anhydride.

4. A process for purifying crude tetrachlorophthalic anhydride containing hexachlorobenzene and iodotrichlorophthalic anhydride impurities, comprising contacting said crude tetrachlorophthalic anhydride with chlorine gas in fuming sulfuric acid or sulfuric anhydride as solvent in the presence of iodine or iodine trichloride, at a temperature ranging from room temperature to 150° C., wherein the quantity of fuming sulfuric acid or sulfuric anhydride is 1 to 20 liters per 1 kg of crude tetrachlorophthalic anhydride and the quantity of iodine or iodine trichloride is 0.1 to 10% by weight as iodine based on the total weight of the reactants, to decompose said hexachlorobenzene impurities, changing the fuming sulfuric acid or sulfuric anhydride solvent to a chlorinated solvent that is one or a mixture of two or more compounds selected from the group consisting of carbon tetrachloride, ethylene tetrachloride, hexachlorobutadiene and benzotrichloride, in an amount ranging from 1 to 100 times by weight of crude tetraphthalic anhydride, and subjecting the reaction mixture to a radical reaction treatment in said chlorinated solvent, at a temperature ranging from room temperature to 150° C., to convert said iodotrichlorophthalic anhydride impurities to tetrachlorophthalic anhydride.

5. A process for purifying crude tetrachlorophthalic anhydride containing hexachlorobenzene and iodotrichlorophthalic anhydride impurities, comprising washing said crude tetrachlorophthalic anhydride with a chlorinated solvent that is one or a mixture of two or more compounds selected from the group consisting of carbon tetrachloride, ethylene tetrachloride, hexachlorobutadiene and benzotrichloride, in an amount ranging from 1 to 100 times by weight of crude tetrachlorophthalic anhydride, at a temperature ranging from 50° to 150° C., to remove said hexachlorobenzene impurities, and subjecting the reaction mixture to a radical reaction treatment in said chlorinated solvent, at a temperature ranging from room temperature to 150° C., to convert said iodotrichlorophthalic anhydride impurities to tetrachlorophthalic anhydride.

6. The process for purifying crude tetrachlorophthalic anhydride as described in claims 1, 2, 3, 4 or 5, wherein said crude tetrachlorophthalic anhydride is a reaction product obtained in the chlorination of phthalic acid, phthalic anhydride or naphthalene.

7. The process for purifying crude tetrachlorophthalic anhydride according to claim 1 or 4, wherein the temperature at which the crude tetrachlorophthalic anhydride is contacted with chlorine gas in fuming sulfuric acid or sulfuric anhydride in the presence of iodine or iodine trichloride is from 50° to 100° C.

8. The process for purifying crude tetrachlorophthalic anhydride according to claim 3, 4 or 5, wherein the temperature of the radical reaction treatment is from 50° to 120° C.

\* \* \* \* \*